US011589795B2

(12) United States Patent
Itah et al.

(10) Patent No.: US 11,589,795 B2
(45) Date of Patent: Feb. 28, 2023

(54) ANNOTATION OF LATE POTENTIALS COMPRISING LOCAL ABNORMAL VENTRICULAR ACTIVATION (LAVA) SIGNALS

(71) Applicant: BIOSENSE WEBSTER (ISRAEL) LTD., Yokneam (IL)

(72) Inventors: Refael Itah, Tel Aviv (IL); Natan Sharon Katz, Atlit (IL); Yaron Kadoshi, Hosha'aya (IL); Gal Hayam, Tivon (IL); Elad Nakar, Timrat (IL); Tal Haim Bar-on, Kiryat Tivon (IL); Eliyahu Ravuna, Kiryat Ata (IL); Lior Botzer, Timrat (IL); Yoav Benaroya, Kfar Saba (IL); Nuno Miguel Rocha Cortez-Diaz, Haifa (PT)

(73) Assignee: Biosense Webster (Israel) Ltd., Yokneam (IL)

( * ) Notice: Subject to any disclaimer, the term of this patent is extended or adjusted under 35 U.S.C. 154(b) by 253 days.

(21) Appl. No.: 17/130,018

(22) Filed: Dec. 22, 2020

(65) Prior Publication Data
US 2022/0192575 A1   Jun. 23, 2022

(51) Int. Cl.
  *A61B 5/366* (2021.01)
  *A61B 5/339* (2021.01)
  *A61B 5/283* (2021.01)
  *A61B 5/28* (2021.01)
  *A61B 5/367* (2021.01)

(52) U.S. Cl.
  CPC .............. *A61B 5/366* (2021.01); *A61B 5/28* (2021.01); *A61B 5/283* (2021.01); *A61B 5/339* (2021.01); *A61B 5/367* (2021.01)

(58) Field of Classification Search
  None
  See application file for complete search history.

(56) References Cited

U.S. PATENT DOCUMENTS

| 5,341,811 A * | 8/1994 | Cano ............... A61B 5/366 600/508 |
| 2007/0021679 A1 | 1/2007 | Narayan |

(Continued)

OTHER PUBLICATIONS

European Search Report for corresponding EPA No. 21216283.8 dated May 18, 2022.

(Continued)

*Primary Examiner* — Kennedy Schaetzle (57) ABSTRACT

A method includes receiving a bipolar signal sensed by a pair of electrodes at a location in a heart of a patient. One or more electrocardiogram (ECG) signals are received, sensed by body-surface electrodes attached to the patient. Two or more successive QRS complexes are identified in the bipolar signal. One or more activations are detected in the bipolar signal, which occur within a window-of-interest that begins at least a given time with respect to the identified QRS complexes. The detected activations are checked whether they are late potentials, by verifying whether (i) the activations do not coincide with a predefined event observed in the ECG signals, and (ii) the activations are repeatable in the successive QRS complexes. In response to deciding that at least one of the detected activations is a late potential, the latest of the at least one of the late potentials is visualized to a user.

26 Claims, 4 Drawing Sheets

(56) References Cited

U.S. PATENT DOCUMENTS

| 2012/0010397 | A1 |   | 1/2012 | Henschke |            |
|--------------|----|---|--------|----------|------------|
| 2012/0101397 | A1 | * | 4/2012 | Blomqvist | A61B 5/0031 |
|              |    |   |        |          | 600/515    |
| 2015/0099992 | A1 | * | 4/2015 | Deno     | A61B 5/283 |
|              |    |   |        |          | 600/516    |
| 2015/0119738 | A1 | * | 4/2015 | Deno     | A61B 5/316 |
|              |    |   |        |          | 600/509    |
| 2016/0128785 | A1 |   | 5/2016 | Nanthakumar |         |
| 2017/0014042 | A1 |   | 1/2017 | Nogami   |            |
| 2017/0156612 | A1 |   | 6/2017 | Relan    |            |

OTHER PUBLICATIONS

Z. M. Yuldashev, et al., "Algorithm for the Abnormal Ventricular Electrical Excitation Detection," *2020 IEEE 14th International Conference on Application of Information and Communication Technologies (AICT)*, 2020, pp. 1-5.

Yuki Komatsu, et al., "*Electrophysiologic characterization of local abnormal ventricular activities in postinfarction ventricular tachycardia with respect to their anatomic location, Heart Rhythm*", vol. 10, Issue 11, 2013, pp. 1630-1637.

\* cited by examiner

ANNOTATION OF LATE POTENTIALS COMPRISING LOCAL ABNORMAL VENTRICULAR ACTIVATION (LAVA) SIGNALS

FIELD OF THE INVENTION

This invention relates generally to electrophysiological (EP) signals, and specifically to a method for evaluation of electrical propagation in the heart.

BACKGROUND OF THE INVENTION

Annotation of electrophysiological signals to determine the local activation times (LATs) was previously suggested in the patent literature. For example, U.S. Patent Application Publication No. 2016/0128785 describes various embodiments for a system and a method for identifying the arrhythmogenic circuit of a patient or subject. In one embodiment, the method comprises obtaining data for electrograms recorded at various locations of the heart while programmed ventricular pacing with extra stimuli to induce ventricular tachycardia (VT) was performed, obtaining decrement values for at least two different locations of the heart using the recorded electrograms, generating at least a portion of a decrement map using the decrement values, and identifying the arrhythmogenic circuit based on electrograms having significant decremental properties. Late potentials, which are local potentials (activations) generally occurring after the end of the QRS complex are reproducibly seen, with reproducible timing from repetitive paced or Sinus Rhythm beats. Abnormal potentials can frequently be seen within the QRS complex (these were coined with the term "left ventricular abnormal local activation," or local abnormal ventricular activity (LAVA)). The issue here is the obvious subjectivity of the operator and the risk that these signals are non-specific targets, hence risking excessive ablation at sites that do not have the properties to induce or sustain re-entrant VT. Accordingly, the areas of late potentials during sinus rhythm (SR) and pacing in both the endocardial and epicardial surfaces were also characterized in the study. Color-coded substrate maps were created with the application of scar mapping and late potentials (LP) mapping during SR and ventricular pacing. The areas of LPs were defined as any local activity after the end of the surface QRS. Very late potentials (VLP) were defined as local activity more than 50 ms from the end of a surface ECG QRS.

As another example, U.S. Patent Application Publication No. 2017/0156612 describes how cardiac activity (e.g., a cardiac electrogram) is analyzed for local abnormal ventricular activity (LAVA), such as by using a LAVA detection and analysis module incorporated into an electro anatomical mapping system. The module transforms the electrogram signal into the wavelet domain to compute as scalogram; computes a one-dimensional LAVA function of the scalogram; detects one or more peaks in the LAVA function; and computes a peak-to-peak amplitude of the electrogram signal. If the peak-to-peak amplitude does not exceed a preset amplitude threshold, then the module can compute one or more of a LAVA lateness parameter for the electrogram signal using one of the one or more peaks detected in the LAVA function and a LAVA probability parameter for the electrogram signal.

SUMMARY OF THE INVENTION

An embodiment of the present invention that is described hereinafter provides a method including receiving a bipolar signal sensed by a pair of electrodes at a location in a heart of a patient. One or more electrocardiogram (ECG) signals are received, that are sensed by one or more body-surface electrodes attached to the patient. Two or more successive QRS complexes are identified in the bipolar signal. One or more activations are detected in the bipolar signal, which occur within a window-of-interest that begins at least a given time with respect to the identified QRS complexes. The one or more detected activations are checked whether they are late potentials, by verifying whether (i) the one or more activations do not coincide with a predefined event observed in the one or more ECG signals, and (ii) the one or more activations are repeatable in the successive QRS complexes. In response to deciding that at least one of the one or more detected activations is a late potential, the latest of the at least one of the one or more late potentials is visualized to a user.

In some embodiments, visualizing the latest late potential includes graphically indicating the latest late potential, in association with the location of the pair of electrodes in the heart, on an electrophysiological (EP) map. In other embodiments, visualizing the latest late potential includes annotating the latest late potential.

In an embodiment, the predefined event includes an activation seen in the one or more ECG signals. In another embodiment, the predefined event includes a fractionation split seen in the one or more ECG signals.

In some embodiments, verifying whether the one or more activations are repeatable includes verifying whether the one or more activations reoccur in at least a given number of heart cycles. In other embodiments, verifying whether the one or more activations reoccur includes using pattern matching.

In an embodiment, the latest late potential includes a local abnormal ventricular activity (LAVA) signal.

In some embodiments, detecting the activations includes applying filtration to smooth the bipolar signal, and detecting in the smoothed bipolar signal one or more activations having an amplitude above a given threshold.

In some embodiments, the received bipolar signal includes a ventricular bipolar signal obtained by catheter electrodes.

In an embodiment, the method further includes receiving a unipolar signal at the location, identifying in the unipolar signal two or more successive QRS complexes. One or more activations are detected in the unipolar signal, which occur within a window-of-interest that begins at least a given time with respect to the identified QRS complexes. The one or more detected activations are checked whether they are late potentials, by verifying whether (i) the one or more activations do not coincide with a predefined event observed in the one or more ECG signals, and (ii) the one or more activations are repeatable in the successive QRS complexes. In response to deciding that at least one of the one or more detected activations is a late potential, the latest of the at least one of the one or more late potentials is visualized to a user.

In some embodiments, checking whether the one or more detected activations are late potentials is performed in real-time.

In some embodiments, the method further includes modifying parameters used in identifying, detecting, checking, deciding, and visualizing the signal.

There is additionally provided, in accordance with another embodiment of the present invention an apparatus including an interface and a processor. The interface is configured to receive a bipolar signal sensed by a pair of electrodes at a location in a heart of a patient, and receive one or more electrocardiogram (ECG) signals sensed by one or more body-surface electrodes attached to the patient. The processor is configured to (i) identify in the bipolar signal two or more successive QRS complexes, (ii) detect in the bipolar signal one or more activations occurring within a window-of-interest that begins at least a given time with respect to the identified QRS complexes, (iii) check whether the one or more detected activations are late potentials, by verifying whether (a) the one or more activations do not coincide with a predefined event observed in the one or more ECG signals, and (b) the one or more activations are repeatable in the successive QRS complexes, and (iv) in response to deciding that at least one of the one or more detected activations is a late potential, visualize the latest of the at least one of the one or more late potentials to a user.

BRIEF DESCRIPTION OF THE DRAWINGS

The present disclosure will be more fully understood from the following detailed description of the embodiments thereof, taken together with the drawings, in which.

DETAILED DESCRIPTION OF EMBODIMENTS

Overview

Ventricular tachycardia (VT) is a heart rhythm disorder (arrhythmia) caused by abnormal electrical signals in the lower chambers of the heart (ventricles). VT may be caused by local electrophysiological (EP) conduction defects in ventricle tissue, such as in scar tissue. To find and treat such arrhythmogenic locations, for example by ablation, the ventricle may be paced and EP mapped using catheters to identify aberrant tissue locations that may be causing the VT.

In particular, EP mapping is done in support of a treatment approach called "scar-homogenization," which has been found useful to ablate scar tissue over an entire area of the scar. The motivation behind the ablative treatment is to target poorly coupled ventricle tissue fibers surviving within a developed scar. These bundles are deemed to generate local abnormal ventricular activities (LAVA) and are believed to be responsible for VT. To this end EP mapping of scar tissue, followed by scar-homogenization, appears to be an optimal procedural endpoint to eliminate all identified LAVA.

Some patients with VT, however, cannot tolerate an extended catheter EP mapping procedure, and this limits the ability to EP map a ventricle to subsequently treat the VT. To complicate matters, efficient identification of the location(s) of conduction defects in a ventricle tissue is particularly challenging for at least two reasons:

Strong ventricular EP activity (manifested in EP signals by the QRS complex) may mask small aberrant EP signals from particular local ventricle sites.

There may be more than one abnormal activation seen in a bipolar intracardiac signal in relationship with a main (QRS) activation, of which only part have clinical significance.

For such reasons, an abnormal activation which should be annotated for EP map generation of an arrhythmogenic ventricle location may be missed by a user.

Embodiments of the present invention that are described hereinafter provide methods and systems to automatically analyze recorded ventricular signals comprising recorded bipolar and unipolar ventricular signals and annotate late potentials in the bipolar or unipolar ventricular signals that can identify LAVA for presentation on an EP map of a ventricle.

These late potentials, of which some are seen against a favorably more quiet background of EP activity, can be analyzed more consistently and efficiently by the disclosed methods.

The disclosed automatic analysis uses two algorithms, which are applied after a main activation point (of a QRS complex) has been annotated. The algorithms are related, one being a general late potential (LP) detection algorithm, and the other, a general LP algorithm adjusted to more robustly detect LAVA, by, for example, considering fractionated QRS complexes in the analysis. For example, the LAVA algorithm eliminates bipolar activation deemed to coincide with a fractionation split seen on the ECG signal.

The LP and LAVA algorithms scan the electrogram waveform from later times (i.e., right of a graph) to shorter times (i.e., left of a graph) after the main annotation, until the scan point meets the main annotation point. The algorithm searches from right to left in a window of interest (WOI) set by the physician, looking for late activation candidates. The LP and LAVA algorithms select the latest occurring bipolar activation candidate which meets certain criteria, such as activations which are consistent (i.e. have a measure of temporal stability) with the previous beat and/or the second previous beat which may also have been determined being of the same activity type (thus overcoming catheter mechanically induced ventricular contractions) and selects the latest activation in the WOI which is consistent over (e.g., occurring also in) the compared beats.

In an embodiment, the processor analyzes successive bipolar and unipolar signals in time, and, if a late occurring bipolar activation is decided as a candidate and repeats itself along prespecified cardiac periods, the processor indicates such a signal as an occurrence of a possibly aberrant localized ventricular activity, for example by annotating the activation. If the processor decides that one or more detected activations are late potentials, the processor visualizes (e.g., on an EP map) only the latest of the at least one of the detected potentials to a user as the LP potential.

Additionally, stability may also be measured by comparing ECG signal morphology (as measured from body surface patches) of the current beat with previous beat(s). In other words, the beats provided by the ECG signals should be consistent (and, by implication, with a same chamber activation sequence) in order to determine late abnormal activations from the bipolar and unipolar intracardiac signals.

Optionally, in order to increase efficiency, the WOI is narrowed (by the physician) to include a region from the right boundary of the WOI to just right of the main annotated activation. This focuses the algorithm on a certain ventricle tissue area, given that the localized signals move temporally depending on where in the ventricle the mapping catheter is positioned.

The disclosed algorithm filters the bipolar signal using measurement of amplitude within a specialized voltage window of interest (also called V-WOI). This amplitude measurement window defines the amplitude of the local signal in mV, which, compared with the reduced QRS amplitude, is of very limited amplitude. The reduced amplitude window is found by searching either side of the annotation to look for "quiet" regions of the signal (with limits on how far to go in search of the "quiet" zones). In this way, the disclosed bipolar signal analysis algorithms eliminate the main activation (i.e. a QRS) from consideration.

Typically, the processor is programmed in software containing a particular algorithm that enables the processor to conduct each of the processor-related steps and functions outlined above.

The disclosed method for the detection of aberrant ventricular activity may improve the safety and value of diagnostic catheterization procedures by enabling a physician to run automatic analysis of diagnostic value.

System Description

Figure 1:
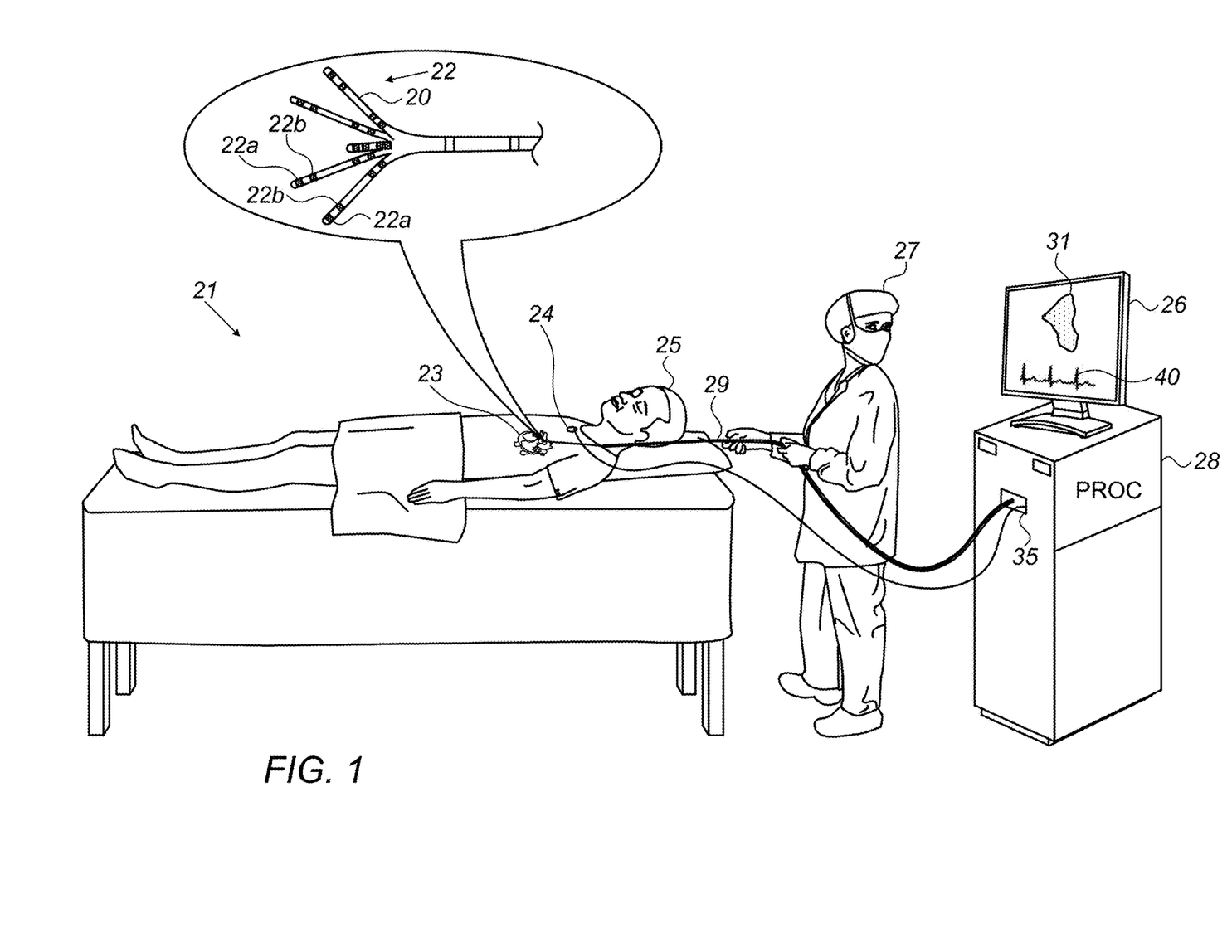
FIG. 1 is a schematic, pictorial illustration of a catheter-based electrophysiological (EP) mapping system, in accordance with an exemplary embodiment of the present invention.

FIG. 1 is a schematic, pictorial illustration of a catheter-based electrophysiological (EP) mapping system 21, in accordance with an exemplary embodiment of the present invention. FIG. 1 depicts a physician 27 using an electro-anatomical mapping catheter 29 to perform an electro-anatomical mapping of a heart 23 of a patient 25. Mapping catheter 29 comprises, at its distal end, one or more arms 20, each of which is coupled to a bipolar electrode 22 comprising adjacent electrodes 22a and 22b.

During the mapping procedure, the locations of electrodes 22 are tracked while they are inside heart 23 of the patient. For that purpose, electrical signals are passed between electrodes 22 and external electrodes 24. For example, three external electrodes 24 may be coupled to the patient's chest, and another three external electrodes may be coupled to the patient's back. (For ease of illustration, only one external electrode is shown in FIG. 1.)

Based on the signals, and given the known positions of electrodes 24 on the patient's body, processor 28 calculates an estimated location of each electrode 22 within the patient's heart. Respective EP data, such as bipolar electrogram traces, are additionally acquired from tissue of heart 23 by using electrodes 22. The processor may thus associate any given signal received from electrodes 22, such as a bipolar EP signal, with the location at which the signal was acquired. The processor 28 receives the resulting signals via an electrical interface 35, and uses information contained in these signals to construct an electrophysiological map 31 and ECG traces 40, and to present these on a display 26.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm as disclosed herein, including in FIG. 4, that enables processor 28 to perform the disclosed steps, as further described below.

The example illustration shown in FIG. 1 is chosen purely for the sake of conceptual clarity. Other types of electro-physiological sensing catheter geometries, such as the Lasso® Catheter (produced by Biosense-Webster Inc., Irvine, Calif.) may be employed. Additionally, contact sensors may be fitted at the distal end of mapping catheter 29 to transmit data indicative of the physical quality of electrode contact with tissue. In an embodiment, measurements of one or more electrodes 22 may be discarded if their physical contact quality is indicated as poor, and the measurements of other electrodes may be regarded as valid if their contact quality is indicated as sufficient.

Figure 2:
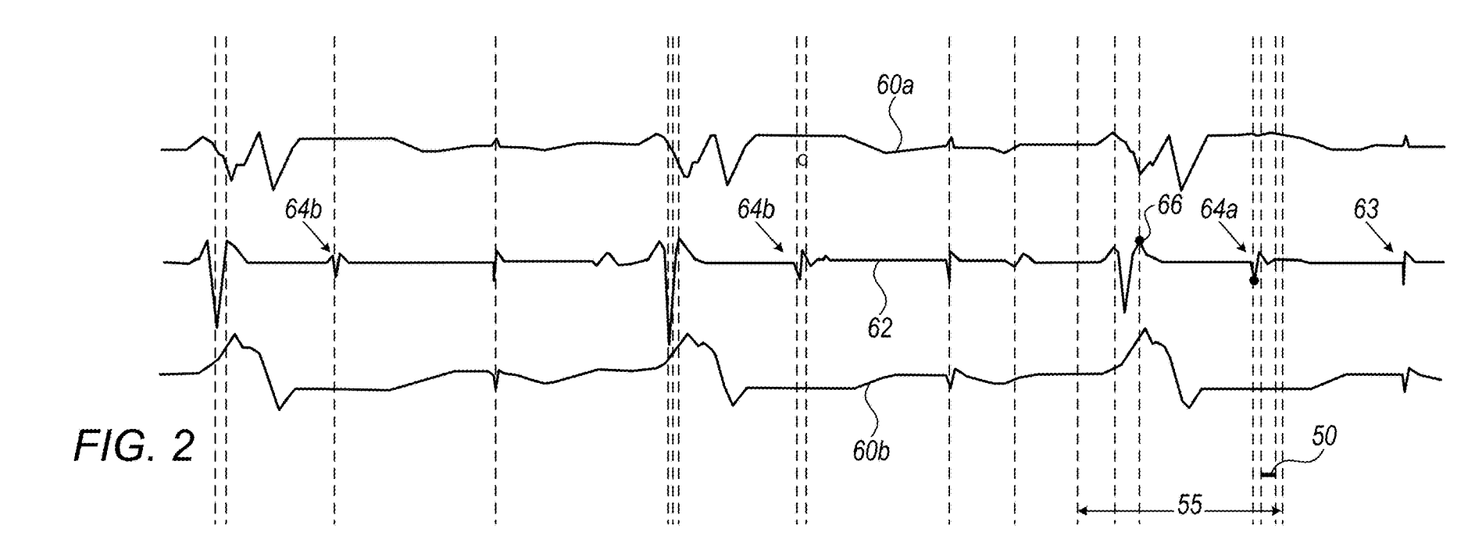
FIG. 2 is a graph of body surface electrocardiograms (ECGs), and bipolar intracardiac electrogram, recorded using the system of FIG. 1, with ventricle activations annotated on the bipolar signal, according to an embodiment of the present invention.

Annotation of Late Potentials Comprising Local Abnormal Ventricular Activation (Lava) Signals FIG. 2 is a graph of body surface electrocardiograms (ECGs) 60a and 60b, and bipolar intracardiac electrogram 62, recorded using system 21 of FIG. 1, according to an embodiment of the present invention. Body surface signals 60a and 60b are received from surface body ECG electrodes, and bipolar signal 62 is received from a pair of electrodes 22 of catheter 29. Late ventricle activations 63, 64a, and 64b are annotated on the bipolar signal. A QRS complex in the bipolar signal 66 is also annotated.

As seen, most correlations are observed between the ECG signals and the bipolar electrogram signal. However, the bipolar electrogram signal may include additional clinically critical information, such as some of the late bipolar activations which have no counterparts in the ECG signal.

Activation 64a falls within a predefined time interval 55 and is identified using a sliding WOI 50 shown within interval 55, all defined by processor 28. The parameters of interval 55 and sliding WOI can be set by a user or by the algorithm, to also consider, for example, activation 63 (which, when analyzed, is found to occur due to atrial pacing, and thus turn out to be irrelevant).

Using sliding WOI 50, processor 28 scans and analyzes, with a late potential algorithm described below, the bipolar electrogram waveform 62 from later times to shorter times after main annotation 66, until the scan point meets the main annotation point. The algorithm searches from right to left in interval 55, looking for late activation candidates. The late potential algorithm selects the latest candidate fulfilling certain criteria:

1. It is not an irrelevant activity (e.g., far field ventricle activity), such as others seen in the ECG signal.
2. The bipolar signal amplitude is above a prespecified threshold.
3. Activations are consistent with the previous beat and/or the next previous beat (i.e. have a measure of temporal stability, as seen by the reoccurrence of signal annotations 64b, which is consistent over the compared beats), and,
4. The latest bipolar activation that meets conditions 1-3 is selected in the WOI.

An additional fifth criterion may be set for stability by comparing ECG signal morphology (as measured from the body surface electrodes, or patches) of the current beat with previous beat(s). In other words, the beats provided by the ECG signal morphology (e.g., line shape) should be consistent (and by that imply a same chamber activation sequence)

in order to be able to draw conclusions about late abnormal activations from the bipolar intracardiac signal.

As seen in FIG. 2, investigated bipolar activation 63 coincides with an ECG activation, and the processor, using criterion 1, eliminates the bipolar activation from further consideration.

By applying criteria 1-4, processor 28 identifies and annotates a candidate late activation indicating aberrant ventricular activity (64a). Additional graphical means and actions taken by processor 28, such as calculating an LAT value for the annotated signal and presenting a respective tissue location on an EP map, are shown in FIG. 5b.

LP and Lava Algorithm Descriptions

The following section describes two variants of the aforementioned algorithms, one for identification of general late potentials (LP), and one optimized for identification of a LAVA sub-group of late potentials. The algorithms search for aberrant ventricle bipolar activation, and, once identified, annotate the activation. In an additional step, the algorithms calculate a bipolar amplitude for the annotated LP/LAVA.

A user has several predefined parameters that affect the general algorithm:

1. Predefined minimal signal amplitude (mV) that is eligible for analysis. The threshold is used as a noise filter.

2. Late potential boundary that defines the right side of the WOI scan (the latest data point in interval 55 considered using the sliding LP-WOI, e.g., WOI 50 in FIG. 2). The late potential boundary function affects the map and its points in the following manner:

i. By default, boundary setting, if applied in real-time during mapping, affects all of the points in a map. A user may change the LP-WOI settings to affect only a selected point or selected group of points.

ii. When multiple points are selected, the LP-WOI boundary can be adjusted and affects only the points selected.

3. The general algorithm finds all of the wavefront (WF) annotation candidates according to the algorithm preferences relating to the WF filter. This step results in candidates for annotation over all of the sampled signals (e.g., over several heart beats), such as annotations 64a and 64b in FIG. 2.

In any given sliding LP-WOI with the range of the interval, the algorithm counts the number of candidates within it. If the number is above X (e.g., X=10 candidates) the algorithm classifies the waveform as a "noisy signal." If the candidate count is above Y (Y>X, e.g. Y=20 candidates) the algorithm classifies the waveform as a "very noisy signal." A waveform portion classified as "very noisy" is dropped from the analysis. For "noisy signal" waveforms, only half, at most (e.g., 5 out of 10), of the found candidates having the strongest dv/dt slopes are used for annotation.

4. The WOI is slid and scanned from its latest border in order to evaluate each WF annotation candidate as a valid LP annotation, up to the LP boundary. If a valid late potential annotation is found it is checked using further criteria as mentioned below. If passed it is marked as an LP annotation site and acquired for addition to an EP map.

5. Once a valid LP annotation, found in the mapping WOI, is defined by the late boundary, the previous two beats in the acquired signal are checked if they meet the criteria, with the previous first beat referred to as "beat-1" and the second beat referred to as "beat-2." The following criteria are checked for the two previous signals, though "passing" the criteria is required only for one of the previous beats:

a. Pattern matching: the two previous beats are checked for matching the pattern of the mapping signal in question defined using the body surface (BS) ECG signal.

b. Timing of a WF annotation candidate in previous beat (beat-1) and one before (beat-2): the two previous beats are checked for the existence of WF annotation candidates in a similar timing frame reference. For beat-1 the accuracy required is within a first time range, $\pm\Delta t_1$, such as $\pm 10$ msec, and for beat-2 the accuracy required is within a first time range, $\Delta t_2$, with typically $\Delta t_2 > \Delta t_1$, such as $\pm \Delta t_2$ being $\pm 20$ msec.

6. Once a valid LP annotation is found to meet the two criteria above, the annotation site is used as a starting point for the late potential bipolar amplitude and, with two optional algorithms below, used to calculate the LP bipolar amplitude:

Option A i. From the LP annotation site, a dynamic V-WOI is calculated over the annotation site. The V-WOI is used to define the signal segment in which the maximum signal amplitude is measured.

ii. The new algorithm explores the annotation site for a "quiet segment" on its two sides and searches for a segment of X msec in the signal that does not change in amplitude more than Y my (by way of example, using current values: X=10 msec and Y=0.02 msec).

iii. The location where the signal meets section 5b condition on both sides of the annotation site defines the borders of section V-WOI in which the signal is measured for the peak-to-peak maximum bipolar amplitude (mv). The measurement of the maximal bipolar is done in the internal segment created by the V-WOI borders.

Option B i. From the annotation site to each side the signal is explored for its amplitude change using a roving segment of "T" msec in which the peak-to-peak amplitude of the signal is measured and checked if it is smaller than the defined "A" minimum amplitude.

ii. If the peak-to-peak value is larger than "A," the roving segment moves 1 msec from the annotation site and performs the above calculation. The process is done on both sides of the annotation site.

iii. If the peak-to-peak value is smaller than "A," the distant border of the roving segment is the V-WOI border (done on both sides of the annotation site). The minimum V-WOI size is 10 msec.

iv. For any instance where the roving segment reaches the "late boundary" or the "mapping WOI," the V-WOI is defined at this site.

7. If no late potential found in the defined LP WOI segment by the late boundary, annotation is searched in the earlier segment of the mapping WOI, meaning from the earlier border of the mapping WOI to the defined late boundary (see below).

a. In this segment a legacy algorithm finds the WF annotation (e.g., having strongest dv/dt), which, if it exists, will be the annotation for this signal in question.

b. For the creation of a voltage map, the bipolar amplitude is calculated in the whole segment (from the earlier border of the mapping WOI to the defined late boundary and/or to the full extent of the WOI) and measured for the peak-to-peak maximum bipolar (mv).

8. If no annotation is found in the signal in question, meaning no LAT value (no-LAT point), no calculation is done for the bipolar value and the point will not support the voltage map.

LP point=An algorithm annotation candidate that is found to be a valid LP point, supporting both the LAT and voltage maps.

LP bipolar value=Maximum peak-to-peak voltage within the defined LP V-WOI.

If an LP signal is not found in the defined LP WOI by the late boundary, then:

LAT LP=N/A

LAT LAVA=Equal legacy LAT (when meeting section 5 conditions)

LAVA V-WOI=Legacy V-WOI

Bipolar LAVA=Maximal peak-to-peak voltage within the LAVA V-WOI

Algorithm Adaptation for Optimized Lava Search

Figure 3:
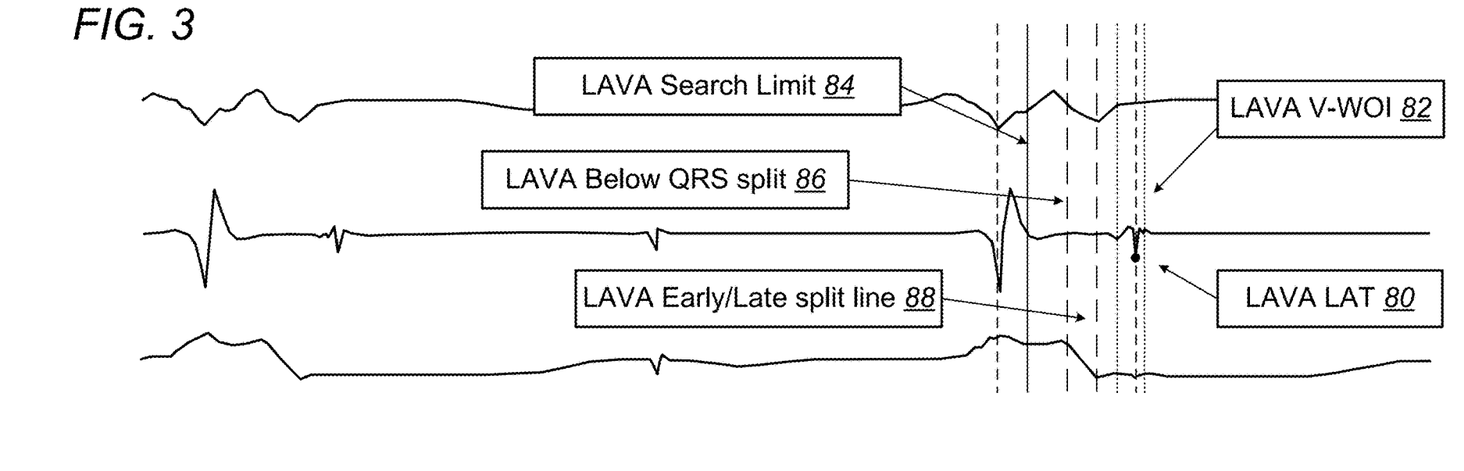
FIG. 3 is a graph of bipolar electrogram and electrocardiogram (ECG) signals analyzed to identify and annotate local abnormal ventricular activity (LAVA), according to an embodiment of the present invention.

FIG. 3 is a graph of bipolar and unipolar electrocardiogram (ECG) signals analyzed to identify and annotate local abnormal ventricular activity (LAVA) 80, according to an exemplary embodiment of the present invention.

A user has several predefined parameters that affect the LAVA detection algorithm:

1. Predefined minimum and maximum signal amplitude (mV) eligible for analysis, in order not to confuse a LAVA signal with the larger Far Field amplitude of a QRS signal and on the other hand not to annotate noise signal smaller than the minimum defined value.

2. User predefined minimal duration of a valid LAVA signal occurring after legacy annotation. An activation point falling below this defined duration is not classified as a LAVA point.

3. Algorithm preference relates to WF filter peak-to-peak value (mV) of a WF.

In order to classify candidate activation as LAVA the following further steps are taken:

4. Setting a V-WOI 82 to measure the bipolar value of the annotated signal.

5. The algorithm defines and classifies the different LAVA signals according to their timing occurrence in WOI using section splits in WOI.

The LAVA search limit 84, available splits beginning Below QRS Split 86 and Early/Late Split line 88.

A user shall be able to change all of the LAVA split lines by dragging Early/Late Split line 88 in the point ECG tool tip—search limit, LV. split and QRS split.

6. The algorithm calculates the time difference (msec) between a legacy signal annotation (e.g., of a QRS complex) and the found LAVA annotation.

7. The WOI is scanned in reverse to evaluate each wave front (WF) annotation candidate to be a valid LAVA annotation, back to search limit 84 or up to a point defined as a blanking area for a LAVA signal (see below).

In case of an area to avoid (a blanking of a noisy area), the algorithm continues to scan prior to the WOI after the skipped blanking area to find a valid LAVA signal.

8. Each WF annotation candidate found is evaluated (in reverse in the defined WOI) to meet a minimum and maximum absolute threshold defined by preferences for a valid LAVA signal.

9. If the LAVA annotation candidate found is equal to the defined time difference (msec) in step 6, the annotation should be the annotation of a legacy signal annotation. If not, the annotation should be the LAVA annotation.

10. The algorithm finds, for each LAVA annotation point, the max peak-to-peak voltage in the defined LAVA bipolar WOI according to these preferences:

a. The max peak-to-peak value in the LAVA signal borders (isoelectric part) according to a defined max noise amplitude and segment of time (msec). The signal borders are defined as very low (less than 0.03 my for a 5 msec period).

b. Defined LAVA V-WOI that opens around the annotation point.

C. The algorithm finds the minimum and maximum peaks to the defined annotation point slope peak-to-peak voltage.

11. Each WF annotation that passes step 4 is evaluated further by:

If LAVA signal is found:

LAT LAVA=WF algorithm annotation candidate that found to be a valid LAVA.

Bipolar LAVA=Max peak-to-peak voltage within the defined bipolar LAVA V-WOI.

If LAVA signal is not found

LAT LAVA=N/A

12. Each WF annotation that passes step 4 is evaluated further by:

If LAVA signal is found:

LAT LAVA=WF algorithm annotation candidate that is found to be a valid LAVA.

Bipolar LAVA=Max peak-to-peak voltage within the defined bipolar LAVA V-WOI.

If LAVA signal is not found

LAT LAVA=N/A

LAT LAVA=Equal legacy LAT (when meeting step 6)

LAVA V-WOI=Legacy V-WOI

Bipolar LAVA=Max peak-to-peak voltage within the LAVA V-WOI

Method of Detection of Late Potentials

Figure 4:
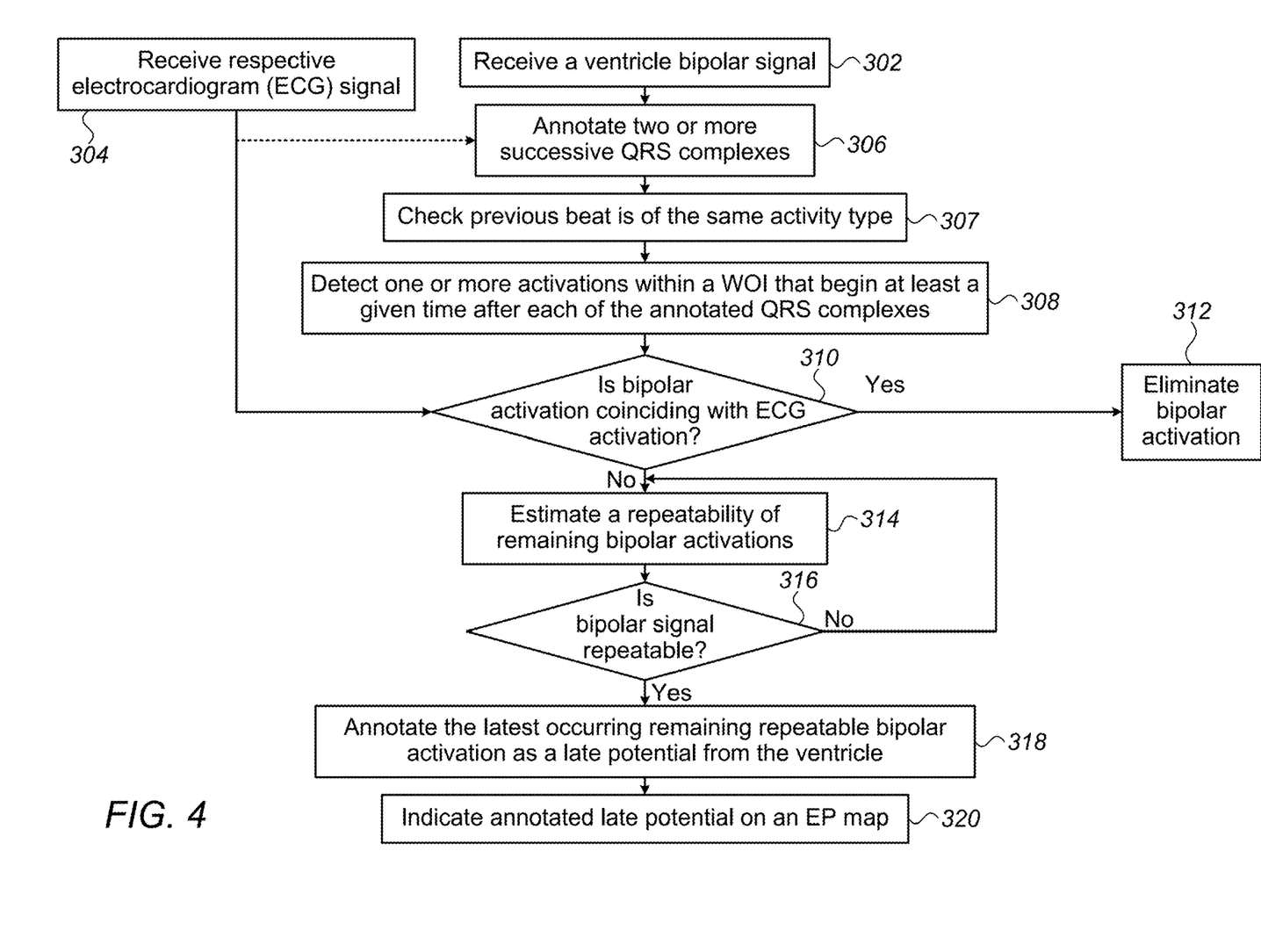
FIG. 4 is a flow chart that schematically illustrates a method and algorithm for the detection of aberrant ventricular activity in bipolar electrograms, according to an exemplary embodiment of the present invention.

FIG. 4 is a flow chart that schematically illustrates a method and algorithm for the detection of aberrant ventricular activity in bipolar electrograms, according to an exemplary embodiment of the present invention. The algorithm, according to the presented embodiment, carries out a process that begins with processor 28 receiving a bipolar signal (e.g., waveform) from catheter 29 at a bipolar data receiving step 302.

At an ECG data receiving step 304, processor 28 receives respective ECG data from a surface electrode.

Next, processor 28 annotates two or more QRS complexes in the bipolar waveform at a QRS annotation step 306. In some cases, if the exact points to annotate the QRS complexes are less evident in the bipolar signal, the processor may use the same annotated locations of the QRS complexes on the ECG waveform.

Next, at an activity type checking step 307, processor 28 checks, according to step 5 of the general algorithm described above, that the previous beat is of the same activity type, for example, using the aforementioned pattern matching method.

Next, processor 28 defines a sliding WOI 50 and operates the algorithm described above to detect one or more activations in the bipolar signal within interval 55, that begin at least a given time after each of the annotated QRS complexes, at a bipolar activation annotation step 308. The detection includes having the algorithm counting the number of candidates within it in order for the algorithm to classify and reject (not shown) noisy signals.

At bipolar activation checking step 310, processor 28 checks if any of the annotated bipolar activations coincide with an ECG activation. If the answer is yes, as seen in activation 63 in FIG. 2, the processor eliminates such bipolar activation from further consideration, at seen in activation elimination step 312. If the answer is no, as seen in activation 64a, the processor estimates the repeatability of the bipolar activation by checking if the activation reoccurs for at least a given number of heart cycles (e.g., by counting a number of activations 64b), at a repeatability checking step 314.

At a checking step 316, processor 28 checks if each of the remaining bipolar activations meets the criteria of step 314. If the answer is no, the processor checks if each of the remaining bipolar activations meets the criteria, by going back to step 314. In an optional embodiment, if no activation that meets the criteria is found, the processor eliminates the bipolar activation from further consideration, by returning to activation elimination step 312.

If the answer is yes, the processor annotates the latest occurring repeatable bipolar activation as a late potential (LP) that originates from ventricle tissue, at a late potential annotation step 318.

Finally, processor 28 indicates the annotated late potential on an EP map, as shown in FIG. 5B, at an EP map generation step 320.

The example flow chart shown in FIG. 4 is chosen purely for the sake of conceptual clarity. The present embodiment may also comprise additional steps of the algorithm, such as receiving multiple bipolar signals and ECG signals simultaneously, as well as receiving indications of the degree of physical contact of the electrodes with diagnosed tissue from a contact force sensor. This and other possible steps are omitted from the disclosure herein purposely in order to provide a more simplified flow chart.

Normal and Abnormal Ventricle Tissue in Ep Maps

Figure 5A:
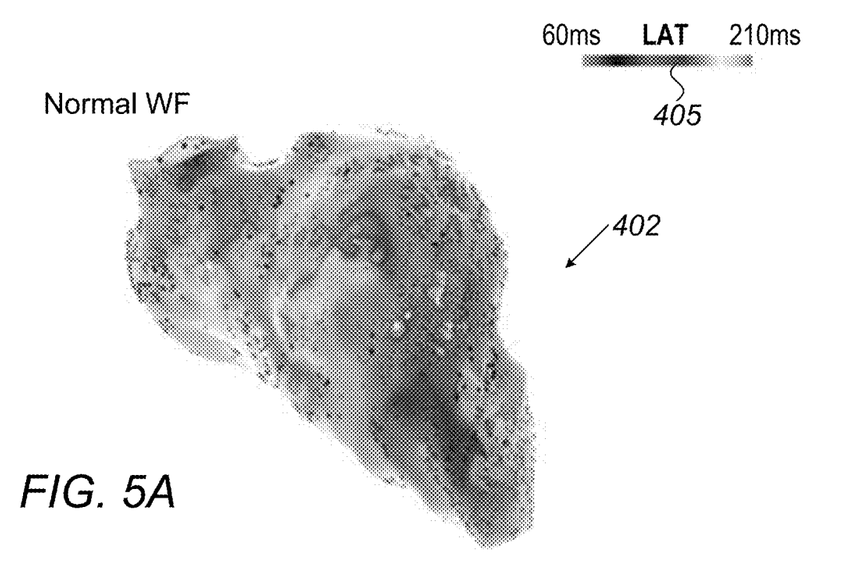
FIGS. 5A and 5B are schematic, pictorial volume renderings of electrophysiological (EP) maps of a ventricle indicating fully normal tissue, and partially aberrant tissue, respectively, according to an exemplary embodiment of the present invention.
Figure 5B:
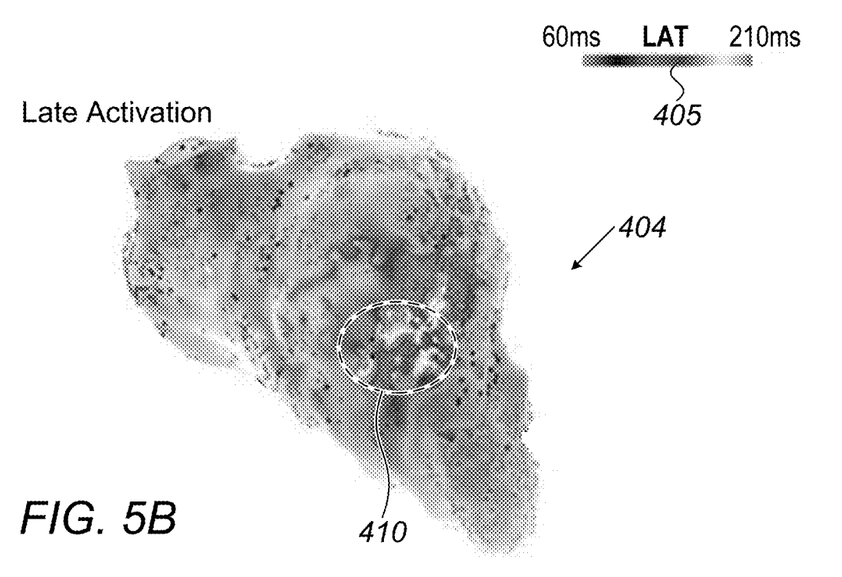

FIGS. 5A and 5B are schematic, pictorial volume renderings of electrophysiological (EP) maps 402 and 404 of a ventricle indicating fully normal tissue, and partially aberrant tissue, respectively, according to an embodiment of the present invention.

FIGS. 5A and 5B show ventricle tissue that is overlaid with color coded local activation times (LATs) using a color scale 405. In the illustrations, grey scale is utilized rather than color. The EP map of FIG. 5B was generated using the above LAVA detection algorithm.

As seen, the surface tissue of ventricle map of FIG. 5A shows a normal EP activation wavefront (WF) as continuous, gradual changes in LAT values, as a normal tissue would demonstrate.

On the other hand, the ventricle map in FIG. 5B shows an isolated area 410, in which LAT values are aberrantly very long, due to late activations. Aberrant tissue area 410 of FIG. 5b is, for example, a scar tissue producing LAVA that would require the aforementioned homogenization treatment by ablation.

As can be seen, the disclosed technique enables a physician to clearly see the occurrence of ventricle tissue area 410 that needs a life-saving invasive treatment using an ablation catheter to eliminate an arrhythmia occurring due to aberrant tissue area 410.

Although the embodiments described herein mainly address cardiac diagnostic applications, the methods and systems described herein can also be used in other medical applications, such as in atrial tachycardia, or in the detection of early potentials by executing the opposite, mirrored algorithm (earliest instead of latest, sliding left to right, instead of right to left).

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for annotation of late potentials comprising abnormal ventricular activation signals, comprising:
   receiving a bipolar signal sensed by a pair of electrodes at a location in a heart of a patient;
   receiving one or more electrocardiogram (ECG) signals sensed by one or more body-surface electrodes attached to the patient;
   identifying in the bipolar signal two or more successive QRS complexes;
   detecting in the bipolar signal one or more activations occurring within a window-of-interest that begins at least a given time with respect to the identified QRS complexes;
   checking whether the one or more detected activations are late potentials, by verifying whether (i) the one or more activations do not coincide with a predefined event observed in the one or more ECG signals, and (ii) the one or more activations are repeatable in the successive QRS complexes; and
   in response to deciding that at least one of the one or more detected activations is a late potential, visualizing the latest of the at least one of the one or more late potentials to a user.

2. The method according to claim 1, wherein visualizing the latest late potential comprises graphically indicating the latest late potential, in association with the location of the pair of electrodes in the heart, on an electrophysiological (EP) map.

3. The method according to claim 1, wherein visualizing the latest late potential comprises annotating the latest late potential.

4. The method according to claim 1, wherein the predefined event comprises an activation seen in the one or more ECG signals.

5. The method according to claim 1, wherein the predefined event comprises a fractionation split seen in the one or more ECG signals.

6. The method according to claim 1, wherein verifying whether the one or more activations are repeatable comprises verifying whether the one or more activations reoccur in at least a given number of heart cycles.

7. The method according to claim 6, wherein verifying whether the one or more activations reoccur comprises using pattern matching.

8. The method according to claim 1, wherein the latest late potential comprises a local abnormal ventricular activity (LAVA) signal.

9. The method according to claim 1, wherein detecting the activations comprises applying filtration to smooth the bipolar signal, and detecting in the smoothed bipolar signal one or more activations having an amplitude above a given threshold.

10. The method according to claim 1, wherein the received bipolar signal comprises a ventricular bipolar signal obtained by catheter electrodes.

11. The method according to claim 1, and comprising:
   receiving a unipolar signal at the location, identifying in the unipolar signal two or more successive QRS complexes;

detecting in the unipolar signal one or more activations occurring within a window-of-interest that begins at least a given time with respect to the identified QRS complexes;

checking whether the one or more detected activations are late potentials, by verifying whether (i) the one or more activations do not coincide with a predefined event observed in the one or more ECG signals, and (ii) the one or more activations are repeatable in the successive QRS complexes; and in response to deciding that at least one of the one or more detected activations is a late potential, visualizing the latest of the at least one of the one or more late potentials to a user.

12. The method according to claim 1, wherein checking whether the one or more detected activations are late potentials is performed in real-time.

13. The method according to claim 1, and comprising modifying parameters used in identifying, detecting, checking, deciding, and visualizing the signal.

14. An apparatus for annotation of late potentials comprising abnormal ventricular activation signals, comprising:

an interface, which is configured to:
receive a bipolar signal sensed by a pair of electrodes at a location in a heart of a patient;
receive one or more electrocardiogram (ECG) signals sensed by one or more body-surface electrodes attached to the patient; and a processor, which is configured to:
identify in the bipolar signal two or more successive QRS complexes;
detect in the bipolar signal one or more activations occurring within a window-of-interest that begins at least a given time with respect to the identified QRS complexes;
check whether the one or more detected activations are late potentials, by verifying whether (i) the one or more activations do not coincide with a predefined event observed in the one or more ECG signals, and (ii) the one or more activations are repeatable in the successive QRS complexes; and
in response to deciding that at least one of the one or more detected activations is a late potential, visualize the latest of the at least one of the one or more late potentials to a user.

15. The apparatus according to claim 14, wherein the processor is configured to visualize the latest late potential by graphically indicating the latest late potential, in association with the location of the pair of electrodes in the heart, on an electrophysiological (EP) map.

16. The apparatus according to claim 14, wherein the processor is configured to visualize the latest late potential by annotating the latest late potential.

17. The apparatus according to claim 14, wherein the predefined event comprises an activation seen in the one or more ECG signals.

18. The apparatus according to claim 14, wherein the predefined event comprises a fractionation split seen in the one or more ECG signals.

19. The apparatus according to claim 14, wherein the processor is configured to verify whether the one or more activations are repeatable by verifying whether the one or more activations reoccur in at least a given number of heart cycles.

20. The apparatus according to claim 19, wherein the processor is configured to verify whether the one or more activations reoccur, by using pattern matching.

21. The apparatus according to claim 14, wherein the latest late potential comprises a local abnormal ventricular activity (LAVA) signal.

22. The apparatus according to claim 14, wherein the processor is configured to detect the activations by applying filtration to smooth the bipolar signal, and detecting in the smoothed bipolar signal one or more activations having an amplitude above a given threshold.

23. The apparatus according to claim 14, wherein the received bipolar signal comprises a ventricular bipolar signal obtained by catheter electrodes.

24. The apparatus according to claim 14, wherein the interface is further configured to receive a unipolar signal at the location, and wherein the processor is further configured to:
identify in the unipolar signal two or more successive QRS complexes;
detect in the unipolar signal one or more activations occurring within a window-of-interest that begins at least a given time with respect to the identified QRS complexes;
check whether the one or more detected activations are late potentials, by verifying whether (i) the one or more activations do not coincide with a predefined event observed in the one or more ECG signals, and (ii) the one or more activations are repeatable in the successive QRS complexes; and
in response to deciding that at least one of the one or more detected activations is a late potential, visualize the latest of the at least one of the one or more late potentials to a user.

25. The apparatus according to claim 14, wherein the processor is configured to check in real-time whether the one or more detected activations are late potentials.

26. The apparatus according to claim 14, wherein the processor is further configured to modify parameters used in identifying, detecting, checking, deciding, and visualizing the signal.

* * * * *